US012588837B2

(12) United States Patent
Wehowski et al.

(10) Patent No.: US 12,588,837 B2
(45) Date of Patent: Mar. 31, 2026

(54) CONTINUOUS ANALYTE SENSOR WITH MAGNETIC ACTIVATION

(71) Applicant: Roche Diabetes Care, Inc., Indianapolis, IN (US)

(72) Inventors: Frederic Wehowski, Hockenheim (DE); Hans List, Oberzent (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1108 days.

(21) Appl. No.: 17/513,378

(22) Filed: Oct. 28, 2021

(65) Prior Publication Data

US 2022/0047188 A1 Feb. 17, 2022

Related U.S. Application Data

(63) Continuation of application No. PCT/EP2020/061572, filed on Apr. 27, 2020.

(30) Foreign Application Priority Data

Apr. 30, 2019 (EP) ..................................... 19171821

(51) Int. Cl.
*A61B 5/145* (2006.01)
*A61B 5/00* (2006.01)

(52) U.S. Cl.
CPC ........ *A61B 5/14503* (2013.01); *A61B 5/0031* (2013.01); *A61B 5/14532* (2013.01); *A61B 5/14546* (2013.01)

(58) Field of Classification Search
None
See application file for complete search history.

(56) References Cited

U.S. PATENT DOCUMENTS

2008/0129486 A1 6/2008 Jeckelmann et al.
2012/0022354 A1* 1/2012 Beyer ................ A61B 5/14503
600/366

(Continued)

FOREIGN PATENT DOCUMENTS

WO WO 2012/050926 A2 4/2012
WO WO 2014/179343 A1 11/2014

OTHER PUBLICATIONS

International Search Report and Written Opinion of the International Searching Authority, PCT/EP2020/061572, Jul. 31, 2020, 10 pages.

*Primary Examiner* — Benjamin S Melhus
(74) *Attorney, Agent, or Firm* — Bose McKinney & Evans LLP

(57) ABSTRACT

An analyte measurement kit includes a sensor assembly having a transcutaneous sensor and a controller. The controller includes a battery that powers the sensor assembly and includes a magnetic sensor that generates an electrical activation signal in dependence of a magnetic field. The controller switches from a pre-operative state into an operative state upon generation of the activation signal. The sensor assembly releasably couples to an inserter. The inserter executes an insertion routine that advances the sensor assembly from a retracted position in which the transcutaneous sensor stands back behind a skin contact surface of the inserter into an advanced position in which the transcutaneous sensor projects beyond the skin contact surface, and subsequently decouples the inserter from the sensor assembly. The inserter includes an activation magnet. Executing the insertion routine changes the magnetic coupling between the activation magnet and the sensor assembly and thereby generates the activation signal.

16 Claims, 4 Drawing Sheets

(56) References Cited

U.S. PATENT DOCUMENTS

| | | | | |
|---|---|---|---|---|
| 2014/0031655 A1* | 1/2014 | Stafford | .............. | A61B 5/6832 |
| | | | | 600/347 |
| 2015/0018643 A1* | 1/2015 | Cole | ................... | A61B 5/6833 |
| | | | | 600/316 |
| 2015/0182153 A1* | 7/2015 | Feldman | ............. | A61B 5/1451 |
| | | | | 600/309 |
| 2020/0337608 A1* | 10/2020 | Garai | ................ | A61B 5/14532 |
| 2020/0337642 A1* | 10/2020 | Garai | ................ | A61B 5/14532 |
| 2023/0026648 A1* | 1/2023 | Cole | ................ | A61B 5/14546 |

* cited by examiner

260

252

100

CONTINUOUS ANALYTE SENSOR WITH MAGNETIC ACTIVATION

RELATED APPLICATIONS

This application is a continuation of PCT/EP2020/061572, filed Apr. 27, 2020, which claims priority to EP 19 171 821.2, filed Apr. 30, 2019, the entire disclosures of both of which are hereby incorporated herein by reference.

BACKGROUND

This disclosure lies in the field of in vivo analyte measurement technology. In particular, it is related to analyte measurement kits for continuous subcutaneous analyte monitoring. The analyte may, for example, be glucose.

The monitoring of characteristic parameters of substances in the human body is crucial for maintaining a healthy state of a person suffering from certain diseases. For example, persons suffering from diabetes mellitus (Persons with Diabetes, PwDs) strongly rely on monitoring glucose concentration in order to avoid hypo- and hyperglycemia. Glucose concentration may be measured in different locations, in particular body fluids such as blood and/or interstitial fluid.

It has long been possible to monitor the blood glucose level with traditional fingerprick testing methods, however these methods only allow the PwD to measure the glucose level at a single point in time (so-called spot measurement). In order to enable continuous monitoring in real time or close to real time, continuous glucose monitoring devices have been developed. In a typical design, a sensor element on electro, electrochemical or enzymatic basis is transcutaneous introduced into the tissue and is connected with an electronic control unit that is carried outside the body, typically via adhesive attachment to the skin. Such combination of sensor element and control unit is in the following generally referred to as sensor assembly. The sensor assembly is typically continuously used for an application time of several days up to several weeks or even months. For introducing the sensor element into the tissue, an insertion device is typically provided.

After the usage time, the PwD can simply remove the sensor assembly from the skin, thereby also withdrawing the sensor element from the tissue. In such design, the sensor assembly is designed as single use device and discarded at the end of its usage time.

The control unit comprises all analogue and/or digital circuitry that is required for the analyte measurements and also a power supply in the form of a battery as discussed further below. The control unit is typically encapsulated in a fully closed and hermetically sealed housing and without any user interface. Measured analyte values and further relevant information (such as status information, error conditions and the like) may be stored in a memory of the control unit and/or transmitted to a remote device via a wireless communication interface. Similarly, data such as calibration data, may typically be received from the remote device via the wireless communication interface. The remote device may, for example, be a dedicated control device, or a general purpose device, in particular a smart phone. Wireless communication may be realized, for example, via Bluetooth®, other general-purpose or proprietary wireless communication means.

In order to provide power for wireless communication as well as overall operation of the device, the control unit contains a small battery. However, the size of the battery and consequently its capacity are limited, as the monitoring devices should be as small as possible for reasons of discreetness and carrying comfort. The usage time of the sensor assembly is, among others, limited by the battery powering the sensor assembly. The battery is typically an integral part of the control unit and cannot be replaced.

Batteries of suitable size and electrical characteristics that have a capacity which is sufficient for providing the power supply for a sensor assembly over its usage time are available. However, the sensor assembly is typically transported and stored in warehouses for extended periods of time of typically several months, potentially even up to several years (referred to as storage time). Thus, any energy that is consumed during the storage time decreases the useful life time of the battery and accordingly of the sensor assembly. For example, some known devices emit every 300 seconds a Bluetooth® signal for finding and connecting to a remote device (pairing). These devices therefore have a very limited storage life time of only up to 3 months. Thus, if the device is stored for a longer period, it may well be that the initial battery capacity is already largely or even completely consumed before the device has even been used for its dedicated purpose. In addition, this type of device has the disadvantage that connecting with the remote device may take up to several minutes, which is known to be annoying for the user.

In view of the above, it is therefore desirable to provide a continuous monitoring system and, in particular, a sensor assembly device with a sensor that is initially, after its manufacture and during storage time, in an inactivated state, where the power consumption is minimal and favorable negligible.

WO 2014/179343 discloses various arrangements for switching from a pre-operative into an operative state. In an embodiment, an activation circuit with an optical sensor is provided which is exposed to light for initializing the sensor electronics. For this type of design, however, suited lighting conditions are required. In another variant, a Reed switch or Hall effect sensor is provided. For initializing the sensor electronics, a magnet is temporarily brought into proximity with the Reed switch or Hall effect sensor. For this type of design, a dedicated user action is required for the initialization process. Further, the initialization may happen unintentionally if the device, and, in particular, the Reed switch or Hall effect sensor, is for any reason exposed to a magnetic field, e.g., due to electromagnetic interference.

WO 2012/050926 discloses the switching of a sensor from a storage mode into a normal operation mode by pulling a magnet away from the sensor electronics module. Thereby an interrupt line is triggered or the state of a Reed switch is altered.

SUMMARY

This disclosure improves the state of the art regarding continuous analyte measurement technology, thereby preferably avoiding the disadvantages of the prior art fully or partly.

Favorably, an analyte measurement kit with a sensor assembly is provided which does not require any or at least only minor amounts of energy in a pre-operative state and which can be readily brought into an operative state by the patient shortly before or during transcutaneous introduction of the sensor. Preferably, little or no additional handling effort for the patient is required. Further favorable, the analyte measurement kit can be manufactured in a cost-efficient manner.

According to a first aspect, an analyte measurement kit including a sensor assembly and an insertion device is disclosed. The sensor assembly comprises a sensor element, preferably a transcutaneous sensor element, and a control unit (also referred to as a "controller"). The control unit includes a battery for powering the sensor assembly, and a magnetic sensor designed or configured to generate an electrical activation signal in dependence of a magnetic field. The control unit is designed or configured to switch from a pre-operative state into an operative state upon generation of the activation signal. The sensor assembly and the insertion device comprise complementary coupling structures for releasable coupling. Furthermore, the insertion device is designed or configured for executing an insertion routine. The insertion routine includes advancing the sensor assembly from a retracted position in which the sensor element stands back behind a skin contact surface of the insertion device into an advanced position in which the sensor element projects beyond the skin contact surface, and subsequent decoupling the insertion device from the sensor assembly. The insertion device includes an activation magnet. Executing the insertion routine is associated with a change of a magnetic coupling between the activation magnet and the sensor assembly, thereby generating the activation signal. The activation magnet is generally a permanent magnet.

An analyte assembly of the above-described type has the advantage that the activation signal is generated during the insertion routine, upon which the control unit is switched from a pre-operative, i.e., inactive, state to an operative, i.e., active, state. It is to be understood that the pre-operative state comprises a state in which no or only marginal battery power is used by the control unit. The pre-operative state may in particular correspond to a low-energy mode or sleep mode of the control unit respectively its circuitry. In the pre-operative state, the control unit has none or only limited function. For example, it is not possible for the control unit in the pre-operative state to communicate with another device, such as a receiving device or to carry out and/or process analyte measurements.

In some embodiments, the change of magnetic coupling may be induced by altering the distance between the activation magnet and the sensor assembly, particularly the magnetic sensor. Alternatively or additionally, a direction of the magnetic field of the activation magnet may be altered, for example by providing a rotatable or turnable activation magnet, such that the activation magnet is rotated or pivoted upon executing the insertion routine. Furthermore, the magnetic coupling may be altered by shielding the magnetic field of the activation magnet from the sensor assembly, in particular, the magnetic sensor. For example, the insertion device may comprise a magnetic shield made, e. g., from a soft ferrite or soft steel, which is brought from an initial non-shielding position into a shielding position upon execution of the insertion routine, or vice versa.

Providing an activation magnet as part of the insertion device and generating the activation signal as consequence of executing the insertion routine is particularly favorable since the insertion routine is a step that needs to be carried out anyway. Therefore, the switching from the pre-operative state into the operative state does not need any particular step to be carried out or measures to be taken by the PwD. Further, the switching is carried out directly at the point in time where it is required, without avoidable delay. That is, upon switching into the activated state, pairing with the remote device can be immediately carried out. In contrast, typical known systems repeatedly emit a signal for detecting the presence of a remote device to connect with during the storage life, i.e., in the pre-operative state. In order to limit the amount of energy that is consumed in the pre-operative state, the time period that lapses between consecutive signal emissions is comparatively long, for example 1 min or even more, resulting in the process being time consuming and often annoying for the user.

As the generation of the activation signal is associated with a change of a magnetic coupling between the activation magnet already present in the insertion device and the sensor assembly, external accidental activation for example during transport may be prevented in some embodiments as explained further below.

The change of magnetic coupling between activation magnet and magnetic sensor may result in an increase or decrease of the magnetic field to which the magnetic sensor is exerted, in dependence of the particular implementation as explained further below. Further, the magnetic field sensor may either be configured to react on the presence respectively strength of a magnetic field, or on a change of the strength of the magnetic field, in particular a time derivative of the magnetic field strength.

Typically, the sensor assembly, in particular the sensor element, comprises one or more electrodes, such as an enzyme-based electrode, which may be based on or include glucose oxidase. The sensor element typically is realized as elongated element, e.g., in form of a rod, wire, or needle, and carries the one or more electrodes that are placed in the subcutaneous tissue respectively interstitial fluid in the insertion routine.

Typically, the sensor assembly comprises an adhesive element, such as an adhesive pad or patch, for skin-mounting the sensor assembly to a patient's skin for an extended time period. The adhesive element may be either directly or indirectly connected to the control unit. For example, the adhesive element may be realized by an adhesive layer or coating that is arranged at a bottom surface of the control unit, in particular a skin contact surface or bottom surface of a sensor housing as explained further below. In the advanced position of the sensor assembly, the adhesive element contacts the skin, thereby fixing the sensor assembly.

Alternatively, an adhesive element, e.g., an adhesive layer or coating, may be provided on a skin contact surface of a separate adapter, commonly also referred to as cradle. Such separate adapter may have a coupling structure for coupling with the sensor assembly which may have a corresponding complementary counter coupling structure. Further, the adapter and the insertion device may comprise complementary adapter-inserter coupling structures for releasable coupling. In such embodiment, the cradle or adapter may be attached to the skin in a first step. Subsequently, the insertion routine is executed in a coupled state of adapter and inserter, thereby coupling the sensor assembly and the cradle or adapter. Subsequently, the insertion device is removed.

In typical embodiments, the insertion device and the sensor assembly are provided readily coupled and in a sterile package. After the insertion process, the insertion device is discarded. Alternatively, however, the coupling of sensor assembly and insertion device via their complementary coupling structures may be established only by the user prior to application. In such embodiment, the insertion device may in principle be reusable.

In some embodiments, the sensor assembly includes a sensor housing, which encapsulates the control unit, wherein the sensor element projects from the sensor housing. In such embodiments, the sensor housing with the control unit may be advanced from the retracted position into the advanced position during the insertion routine by the insertion device together with the sensor element. In executing the insertion routine, the sensor element pierces the skin of the PwD and gets introduced into the tissue, such that the one or more electrodes are placed in the subcutaneous tissue or interstitial fluid. Further in the advanced position, an adhesive layer or coating on the bottom surface of the sensor housing rests on the skin of the PwD, thereby fixing the control unit on the skin. Alternatively, the sensor assembly may, when assuming the advanced position, couple with an adaptor or cradle via complementary coupling structures as explained before. The sensor element may project perpendicularly from the bottom surface of the housing. For such design, the insertion movement is generally perpendicular to the skin. In alternative designs, the sensor element and the plane that defines the bottom surface have an angle in a range, of, e.g., 30 to 60 degrees. For such embodiment, the insertion movement is generally inclined or oblique with respect to the skin surface.

In some embodiments, the insertion device further includes an elongated piercing element, which is structurally coupled with the sensor element in the retracted position. The insertion routine includes advancing the piercing element together with the sensor assembly from the retracted position into the advanced position, followed by only retracting the piercing element into the retracted position. This kind of embodiment is particularly favorable if the sensor element that is introduced into the tissue is flexible respectively not sufficiently stiff to pierce the skin without bending or cranking and/or has a blunt rather than a pointed tip. The piercing element, in contrast is stiff and pointed to be easily pushed through the skin. During the insertion routine, the piercing element remains coupled with the sensor element, such that the sensor element is guided into the tissue together with the piercing element and stabilized by the piercing element. The piercing element and the sensor element are favorable in mechanical contact over substantially their whole length, e.g., in a side-by-side arrangement in a coaxial arrangement with the sensor element being arranged in a central lumen of the piercing element. Alternatively, the sensor element may be hollow and have a central lumen in which the piercing element is arranged. The piercing element may be an insertion needle or a cannula and may be decoupled from the sensor element before retraction of the piercing element. In alternative embodiments, however, the sensor element may be sufficiently stiff to pierce the skin and be introduced into the tissue without requiring an additional piercing element.

In some embodiments, the insertion device includes an insertion device housing. The activation magnet is rigidly coupled to the insertion device housing. In dependence of the position of the activation magnet, different kinds of embodiments may be realized regarding the magnetic coupling and the change thereof when executing the insertion routine, as explained in the following.

In some embodiments, the activation magnet is positioned such that the distance between the activation magnet and the magnetic sensor increases upon advancing the sensor assembly, in particular the magnetic sensor, into the advanced position, thereby generating the activation signal. Increasing the distance between the activation magnet and the magnetic sensor results in a continuous reduction of the magnetic coupling between the activation magnet and magnetic sensor and accordingly a continuous reduction magnetic field strength at the magnetic sensor. For such type of embodiment, the activation magnet is positioned, e.g., by attaching to an insertion device housing, in a position where it is in close vicinity to the magnetic sensor in the retracted position, resulting in the magnetic coupling being maximal in the initial retracted position of the sensor assembly. For this type of embodiment, magnetic sensors that react on the strength and/or a change in the magnetic field may be used. The latter is particularly favorable in typical embodiments where the insertion device includes one or more resilient elements, such as an arrangement of one or more springs, for quickly moving the sensor assembly from the retracted into the advanced position. The movement typically result in a sufficient change in the magnetic field (time derivative of the magnetic field strength) for the magnetic sensor to react and generate the activation signal. It is noted that the larger the change in the magnetic field strength, the less sensitivity is required for the magnetic sensor. A comparatively low sensitivity is favorable since it results in the design being less critical and the tolerance with respect to interfering magnetic fields is reduced.

In some embodiments, the activation magnet is positioned such that a distance between the activation magnet and the magnetic sensor decreases upon advancing the sensor assembly into the advanced position, thereby generating the activation signal. Decreasing the distance between the activation magnet and the magnetic sensor results in a continuous increase of the magnetic coupling between the activation magnet and magnetic sensor and accordingly a continuous increase of the magnetic field strength at the magnetic sensor. For such type of embodiment, the activation magnet is positioned, e.g., by attaching to an insertion device housing, in a position where it is close vicinity to the magnetic sensor in the advanced position, resulting in the magnetic coupling being maximal in the advanced position of the sensor assembly. This type of embodiment is in principle similar to the before-described type of embodiment but complementary in that the magnetic coupling increases rather than decreasing when moving the sensor assembly from the retracted into the advanced position.

In a further type of embodiment, the change in magnetic coupling and accordingly the generation of the activation signal occurs as decrease and finally canceling of the magnetic coupling upon detaching and removing the insertion device at the end of the insertion routine. In such embodiment, the activation magnet may be arranged at the inserter device housing in a position where it is in close vicinity to the magnetic sensor in the advanced position as in the before-discussed type of embodiment. Similarly, the activation magnet may be arranged at or in the coupling structure of the insertion device for coupling with the sensor assembly.

In some embodiments, the activation magnet is coupled with the piercing element to move relative to the sensor assembly when retracting a piercing element as explained before into the retracted position. In embodiments in which the retraction is performed rapidly, for example by a resilient element, such as a spring, the change rate of the magnetic coupling is large. Therefore, the required sensitivity of the magnetic sensor is decreased and the occurrence of malfunctions is reduced as also explained before. For this type of embodiment, the activation signal is generated when retracting the piercing element subsequent to placing the sensor element into the tissue.

In some of the before-described embodiments, the activation magnet is rigidly coupled to or included in the piercing element. If the activation magnet is included in the piercing element, no additional structural features, which further complicate the overall setup of the analyte measurement kit, are required. The piercing element may for example partially or fully be made from a permanent magnetic material.

In some embodiments, the magnetic sensor includes a coil. The coil may, e.g., be a planar coil and be realized as part of a printed circuit board of the control unit. Alternatively, the coil may be an elongated cylindrical coil. This type of embodiment is based on the fact that a voltage is induced in a coil if the magnetic flux through the coil changes, with the voltage serving as activation signal. Favorably, the coil is connected to a microprocessor or microcontroller of the control unit, e.g., at an interrupt port or wake-up port. Since the voltage is proportional to the first time derivative of the magnetic field in accordance with the law of induction, this type of embodiment is particularly favorable in embodiments where the magnetic coupling between activation magnet and magnetic sensor changes quickly, e.g., in a spring-driven advancement of the sensor assembly from the retracted into to the advanced position or a spring-driven retraction of a piercing element. In all of these embodiments, the voltage that is induced in the coil and serves as activation signal is peak-respectively pulse shaped. A particular advantage of using a coil as magnetic sensor in the present context is that the voltage that serves as activation signal is generated by the coil and accordingly no further power supply is needed for powering the magnetic sensor, which is favorable regarding the desired minimal power consumption during storage and prior to usage. The magnetic field, however, needs to be comparatively strong.

In some embodiments, the magnetic sensor includes a Hall effect sensor. As known in the art, a Hall effect sensor measures strength of a magnetic field to which the sensor is exerted. In contrast to a coil as explained before in the context of other embodiments, a Hall effect sensor reacts on the strength of a magnetic field rather than its rate of change and is capable of measuring both static and changing (dynamic) magnetic fields. The use of a Hall effect sensor is accordingly particularly favorable where the change in magnetic coupling between activation magnet and magnetic sensor is comparatively slow. State-of-the-art Hall effect sensors are typically realized as micro-machined semiconductor components. It is noted that, in order to detect the change in magnetic coupling with the activation magnet, the Hall effect sensor needs to be continuously powered via a DC power supply. However Hall effect sensors are available that only require a current of about 350 nA to operate. When using such Hall effect sensor, a standard small coin cell battery as power supply of the sensor assembly is depleted only to a small degree during the storage time of several months up to years, such that sufficient battery capacity remains for powering the sensor assembly during its application time. In a further embodiment, a Reed switch is provided as magnetic sensor which opens and closes in dependence of a magnetic field. A particular advantage of a Hall effect sensor or Reed switch is that the magnetic field can be comparatively week. Therefore, the activation magnet can be small and cheap. For example, the activation magnet may be a resin-bound magnet.

In some embodiments, the activation magnet and the magnetic sensor are aligned, in particular coaxially aligned, with each other in a coupled state of the senor assembly and the insertion device. This type of arrangement favorably maximizes the magnetic coupling. For embodiments where the magnetic sensor is a coil, the relative arrangement of activation magnet and coil is favorably such that the magnetic flux lines are parallel to the coil axis for maximum magnetic coupling, In embodiments where the magnetic sensor is a Hall effect sensor, the arrangement is favorably such that the magnetic flux lines correspond to a direction of maximum sensitivity of the Hall effect sensor (perpendicular to a plane as defined by the Hall probe of the Hall effect sensor).

In some embodiments, the control unit includes a wireless communication interface. Furthermore, the control unit is configured to pair with a remote device for data communication via the wireless communication interface upon being switched into the operative state. In particular, the remote device may include a smart phone, a portable computer or any other suitable device. In alternative embodiments, it may also be possible to connect the control unit via a communication interface and a cable with a device for data communication.

In some embodiments, the sensor assembly is configured to execute analyte measurements in the operative state, for example, by electrochemical or electroenzymatic measurements. In some particular embodiments, the analyte is glucose. In the pre-operative state, in contrast, no analyte measurements are carried out and the control unit is in a low-energy or sleep mode and only the magnetic sensor is powered (in case of the magnetic sensor being a Hall effect sensor as explained before) and those parts of the control unit, in particular of a microcontroller or microprocessor, that are required for detecting the generation of the activation signal and reacting thereon. In the operative state, the control unit may be configured to directly transmit glucose measurements to the remote device, and/or to temporarily store measurement results in a memory of the control unit and transmit them upon request by the remote device and/or according to a transmission time schedule.

According to a further aspect, a method is provided for switching a sensor assembly from a pre-operative state in an operative state. The method includes: (a) providing an analyte measurement kit according to any of the embodiments described herein; and (b) executing an insertion routine, the insertion routine including changing a magnetic coupling between the activation magnet and the sensor assembly, thereby generating the activation signal.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
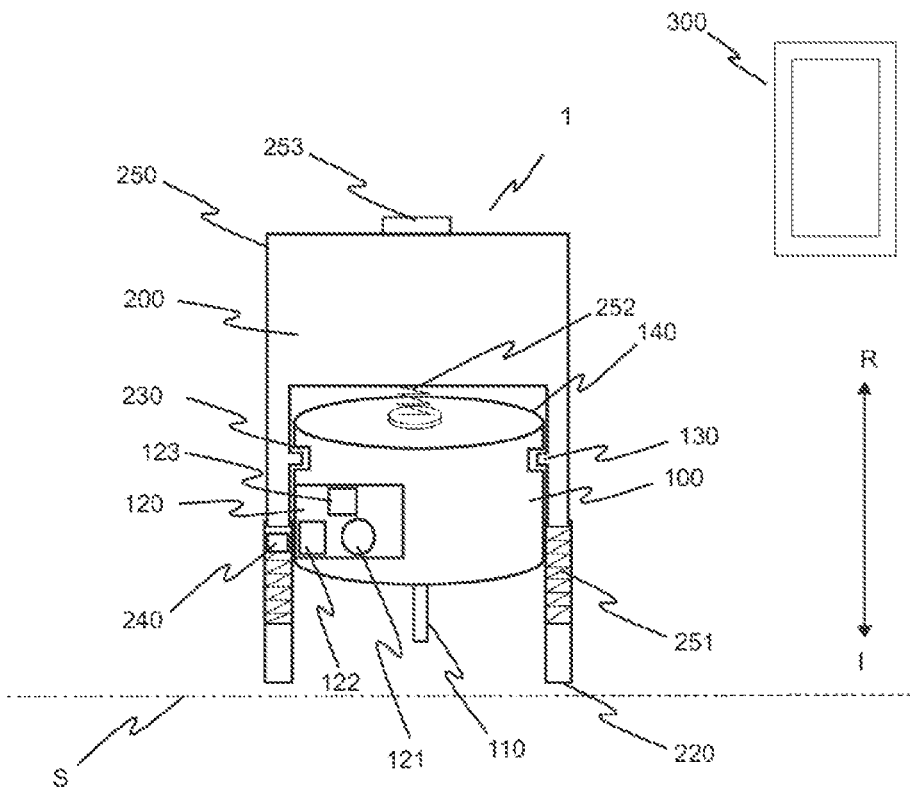
FIG. 1 shows a schematic view of an analyte measurement kit in accordance to a first.

The analyte measurement kit 1 shown in FIG. 1 includes a sensor assembly 100, which is releasably coupled with an insertion device 200 via corresponding coupling structures (also referred to herein as "couplers") 130 and 230. Sensor assembly 100 comprises control unit (also referred to herein as a "controller") 120 and sensor element (also referred to herein as "transcutaneous sensor" or "sensor") 110. Furthermore, sensor assembly 100 is encapsulated in sensor housing 140, while sensor element 110 protrudes or projects from the sensor housing 140. Control unit 120 includes a battery 121 for powering the sensor assembly 100 and a magnetic sensor 122, which is designed to generate an electrical activation signal in dependence of a magnetic field and may be either of a Hall effect sensor or a coil. The sensor assembly 100 is shown in its retracted position prior to insertion of the sensor element 110 into the patient's skin S and thus the control unit is in a pre-operative state. Insertion device 200 is designed for executing an insertion routine, the insertion routine including advancing the sensor assembly 100 from the shown retracted position, where the sensor element 110 stands back (or is recessed) behind a skin contact surface 220 of the insertion device 200 along insertion direction I into an advanced position in which the sensor projects beyond the skin contact surface 220. Afterwards, the insertion device 200 is decoupled from sensor assembly 100 by releasing the coupling of coupling structures 130 and 230. The insertion device 200 includes an activation magnet 240, which in the embodiment at hand is rigidly coupled to insertion device housing 250 in a fixed position. Housing 250 comprises resilient element 251, which is contracted at the beginning of the insertion routine and which is expanded after the sensor element 110 has protruded the skin and the sensor assembly 100 and the insertion device 200 have been decoupled. Furthermore, housing 250 comprises spring element 252, which is contracted and thus loaded at the beginning of the insertion routine. If the user operates activator 253, which may be a push button, spring 252 is unloaded and the sensor assembly is advanced in an advanced position upon which resilient assembly 251 is contracted and thus loaded. In the present embodiment, activation magnet 240 and magnetic sensor 122 are coaxially aligned in the coupled state shown in FIG. 1. If the insertion routine is executed, i.e., when the sensor assembly 100 is brought into the advanced position, the sensor assembly 100 and thus the magnetic sensor 122 is moved away relative to the activation magnet 240. Thus, in the embodiment shown, a distance between the activation magnet 240 and the magnetic sensor 122 increases upon executing the insertion routine, i.e., upon advancing the sensor assembly into an advanced position. Consequently, the magnetic coupling between activation magnet 240 and magnetic sensor is reduced and finally cancelled. Thereby, the activation signal is generated, upon which the control unit is switched from a pre-operative to an operative state. Control unit 100 further comprises wireless communication interface 123, with which the control unit 120 can be paired with remote device 300 for data communication, when the control unit is switched into the operative state.

Figure 2:
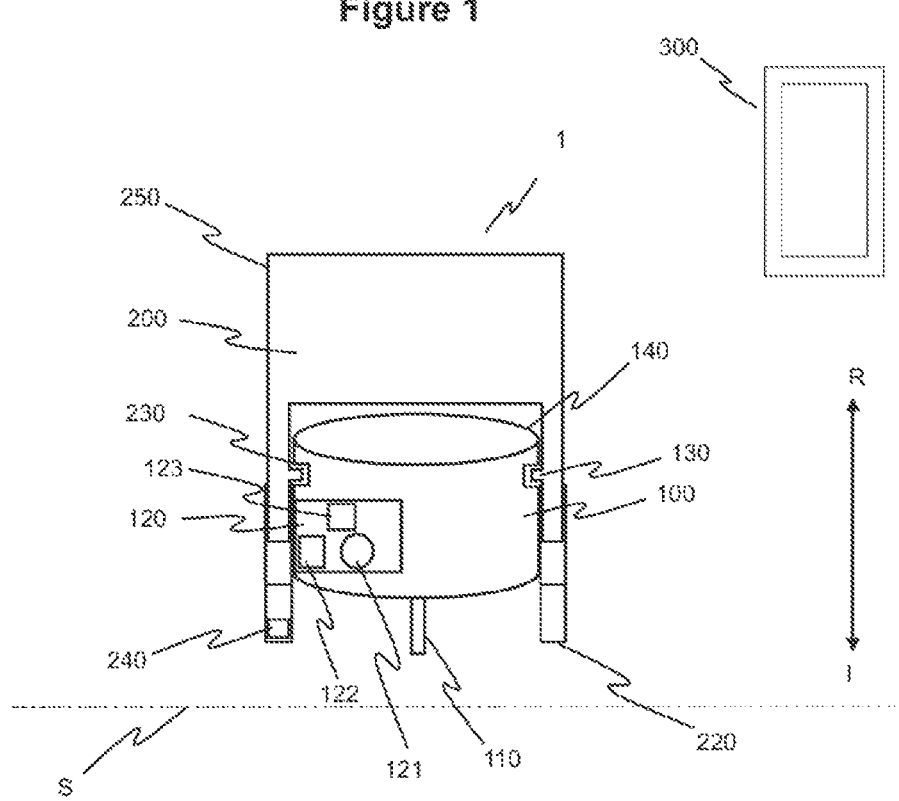
FIG. 2 shows a schematic view of an analyte measurement kit in accordance to another embodiment.

FIG. 2 shows another embodiment of an analyte measurement kit 1. The analyte measurement kit 1 also includes sensor assembly 100, which is coupled to insertion device 200 via complementary couplers 130 and 230. Compared to the embodiment shown in FIG. 1, insertion device 200 includes activation magnet 240, which is however arranged at a different position, i.e., in close proximity of skin contact surface 220. FIG. 2 shows the coupled analyte measurement kit 1 during the insertion routine. The insertion device 200 is already compressed to a certain level as compared to the embodiment shown in FIG. 1, for example by a pressure exerted by the patient on the top surface of insertion device housing 250 and sensor assembly 100 is advanced in the insertion direction I. In the particular embodiment shown, the two legs of the insertion device slide into each other, which brings the sensor assembly 100 in an advanced position in which sensor element 110 can protrude from the skin contact surface 220 and puncture the patient's skin S. Concomitantly, the distance between the magnetic sensor 122 and the activation magnet decreases. In this embodiment, the magnetic coupling between the sensor assembly 100 and activation magnet 240 changes and thereby generates the activation signal, because the distance between the sensor assembly 100 and activation magnet 240 decreases upon advancing the sensor assembly into the advanced position. Like in the embodiment of FIG. 1, the magnetic sensor 122 may be either of a Hall effect sensor or a coil.

Figure 3:
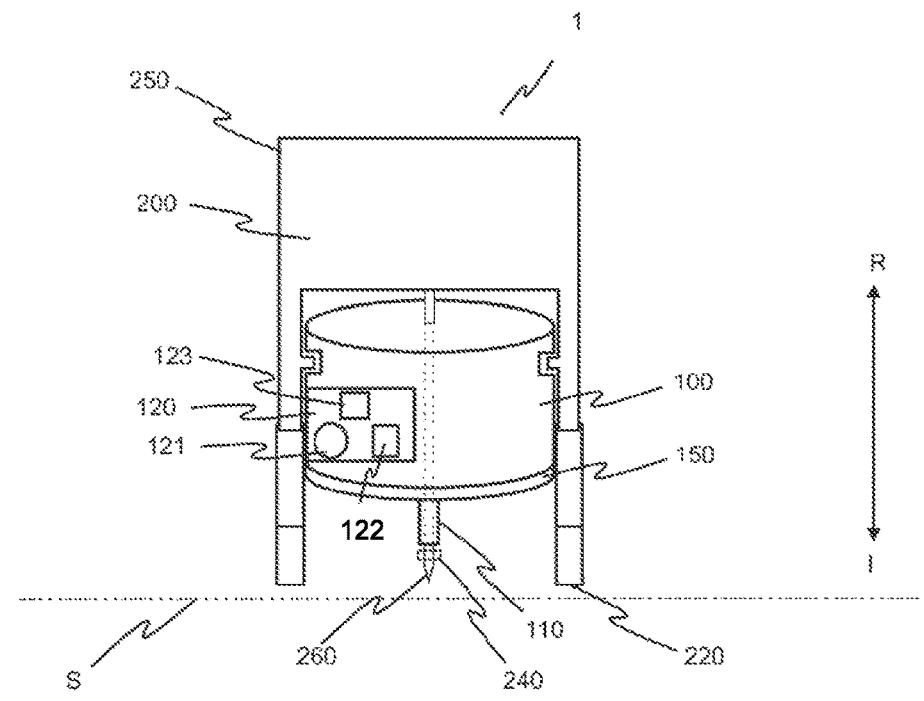
FIG. 3 shows a schematic view of an analyte measurement kit in accordance to another embodiment.

FIG. 3 depicts another embodiment of an analyte measurement kit 1. Analyte measurement kit 1 comprises sensor assembly 100 with sensor element 110 and control unit 120. Furthermore, the sensor assembly 100 comprises an adhesive element 150, such as an adhesive pad, at the lower surface for skin-mounting the sensor assembly 100 to the patient's skin for an extended period of time. Analyte measurement kit 1 further comprises insertion device 200 with insertion device housing 250 and skin contact surface 220. In contrast to the embodiments shown in FIGS. 1 and 2, the insertion device 200 additionally comprises piercing element 260, which is structurally coupled with sensor element 110. For example, sensor element 110 can be tubular and/or cylindrical, and the piercing element is circumferentially encompassed by sensor element 110. Furthermore, activation magnet 240 (drawn in exaggeration, for better illustration) is rigidly coupled to piercing element 260. During the insertion routine, piercing element 260 is advanced together with sensor assembly 100 from the retracted position in insertion direction I into the advanced position, followed by retraction of only piercing element 260 into the retracted position in retraction direction R, while the sensor assembly 100 remains in the advanced position. For example, the insertion routine may comprise a decoupling step, in which the structural coupling of sensor element 110 and piercing element 260 is released. Thus, while upon advancing the sensor assembly together with the piercing element and the activation magnet does not entail a change in magnetic coupling between activation magnet 240 and sensor assembly 100, retracting only the piercing element 260 together with the activation magnet 240 does trigger a change in magnetic coupling, which generates an activation signal. Thereby control unit 120 is switched from a pre-operative state in an operative state, in which it may communicate with remote device via communication interface 123. It is noted that a piercing element 260 may also be present in the other embodiments, where it is, however, not involved in generating the activation signal.

In the embodiments of FIG. 1 to FIG. 3, the magnetic sensor 122 may also be realized as Reed switch. In the embodiment of FIG. 1, the advancement movement of the sensor assembly results in the distance between the activation magnet 240 and the magnetic switch increasing, thereby opening the Reed switch. The same holds true for an embodiment according to FIG. 3. In the embodiments of FIG. 2, in contrast, the decreasing distance to the activation magnet results in the Reed switch being closed as result of the sensor assembly 100 moving from the retracted into the advanced position.

FIG. 4 to FIG. 7 show a further embodiment of the analyte measurement kit 1. A base part 202 is received in the cap part 201 and is displaceable with respect to the cap part 201 in a telescopic manner along the insertion direction. Similarly, the piercing element carrier 203 is received in the cap part 201 in a coaxial manner as explained further below. The piercing element carrier 203 is displaceable with respect to the cap part 201 along the insertion direction. The piercing element carrier 203 carries piercing element 260 that projects from the piercing element carrier 203 (best visible in FIG. 6).

Figure 4:
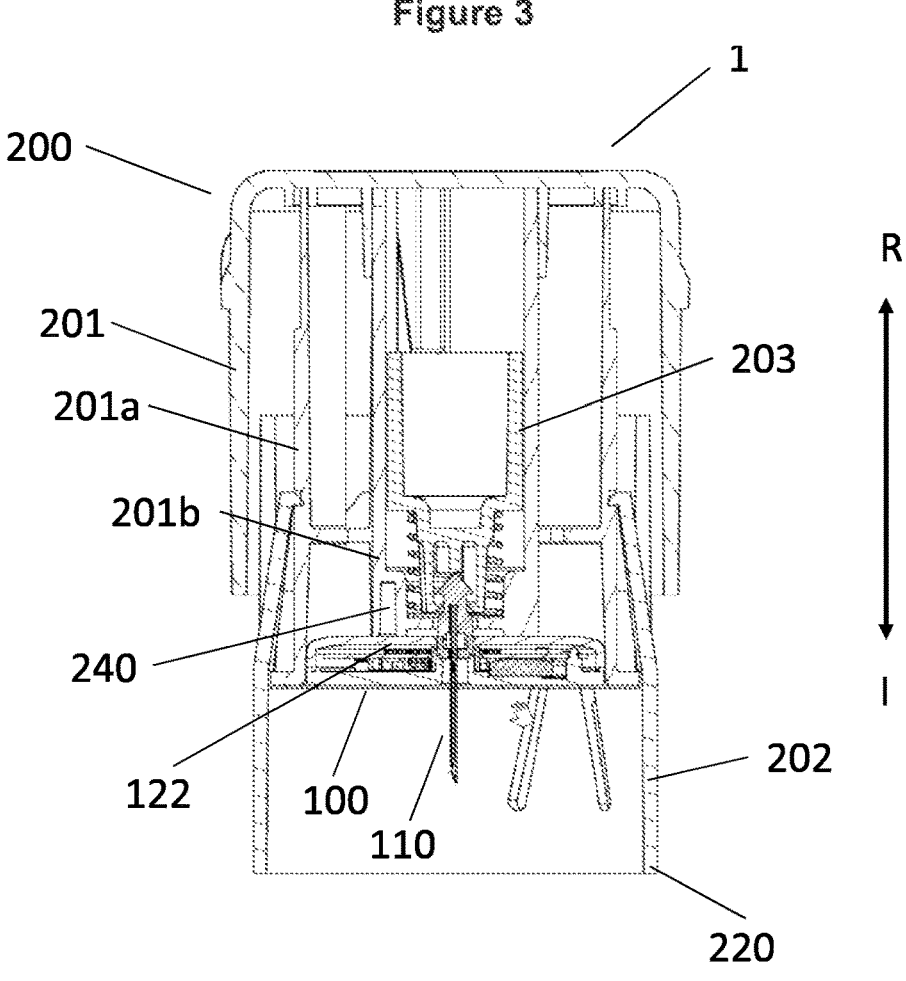
FIG. 4 shows a further embodiment in a first configuration.

A sensor assembly carrier 201a projects from the top wall of the cap element 201 and is connected at its lower skin-facing side to the sensor assembly 100 which is further circumferentially surrounded by the sensor assembly carrier 201a. The sensor assembly carrier 201a is rigidly connected to the cap element 201 and may be considered as a functional part thereof. FIG. 4 shows an initial configuration where the base part 202 projects beyond the cap part 201 at the lower side towards the skin S. Further, the base part 202 is releasably locked against the cap part 201. The sensor element 110 projects from the skin-facing side of the sensor assembly 100 and stands back behind the skin contact surface 220. Further, a generally tubular piercing element carrier guide 201b projects from and is rigidly connected with the top portion of the cap element 201. The piercing element carrier guide 201b may be considered as functional component of the cap element 201. In its inner space, the piercing element carrier guide 201b receives the piercing element carrier in a longitudinally displaceable manner. Further, the piercing element carrier guide 201b carries at its outside locking structures for locking the base part 202 in two alternative positions (see, e.g., FIGS. 4, 5). The piercing element carrier guide extends towards the top surface of the sensor assembly 100.

Figure 5:
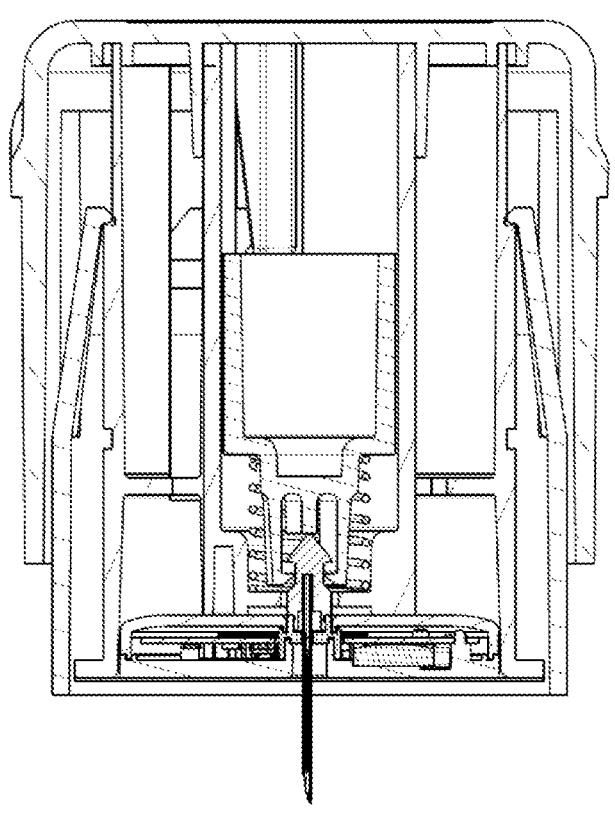
FIG. 5 shows a further embodiment in a second configuration.

Insertion is carried out by placing the skin contact surface 220 on the skin and manually pressing down the cap element 201. Thereby, the locking between cap element 201 and base part 202 is released. Consequently, the cap part 201 and the sensor assembly 100 move downwards. In an inserted configuration, the base part 202 is again locked against the cap part 201. In this inserted configuration, the sensor element 110 is introduced into the skin and the sensor assembly is placed on the skin. The inserted configuration is shown in FIG. 5.

Figure 6:
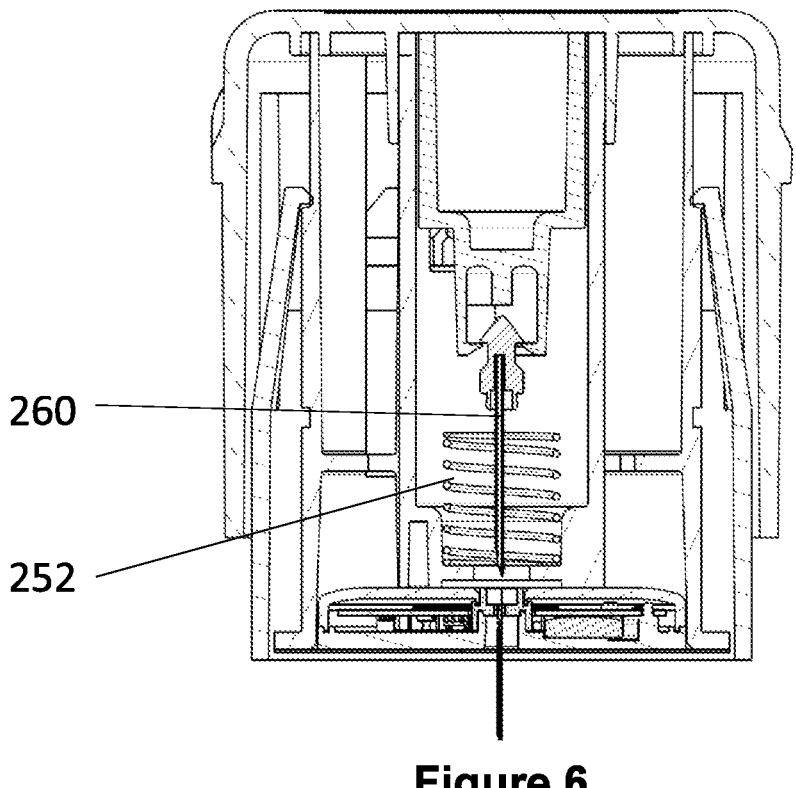
FIG. 6 shows a further embodiment in a third configuration.
Figure 7:
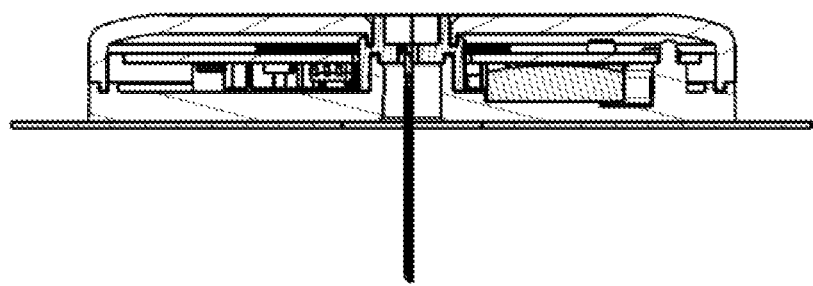
FIG. 7 shows the sensor assembly of the embodiment of FIG. 4 to FIG. 6 after removal of the insertion device.

In the end configuration, pressing down the cap element 201 by the user is released. As best visible in FIG. 6, a compression spring 252 is arranged between the base element 202 and the piercing element carrier 203. In the initial configuration (FIG. 4), spring 252 is released. In moving from the initial configuration to the end configuration (FIG. 5), spring 252 is compressed and accordingly stressed. When releasing the cap element 201 in the configuration of FIG. 5, spring 252 is unstressed, thereby pushing the piercing element carrier 203 upwards. Since the piercing element 260 is rigidly connected to the piercing element carrier 203, it also moves upwards and the piercing element 260 is retracted. This configuration is shown in FIG. 6. FIG. 7 shows the sensor assembly 100 in a situation of use, after decoupling and removing the insertion device 200.

The activation magnet is arranged in the piercing element carrier guide 201b in close proximity to the top surface of the sensor assembly 100 and laterally spaced apart from the central axis. The magnetic orientation corresponds to the insertion direction. Consequently, the magnetic flux passes through the sensor assembly 100. The magnetic sensor 122 is a Hall effect sensor that is arranged with its active surface according to the magnetic flux of the magnet 240. During the whole storage time and until the insertion device 200 is removed (transition from FIG. 6 to FIG. 7), the magnetic flied is continuously sensed by the magnetic sensor 122. With removal of the insertion device 200, the magnetic field of the activation magnet 240 is no longer detected, causing the sensor assembly 100 to switch from the pre-operative state into the operative state.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF DESIGNATIONS

1 Analyte measurement kit
100 Sensor assembly
110 Sensor element
120 Control unit
121 Battery
122 Magnetic sensor
123 Wireless communication interface
130 Coupling structure
140 Sensor housing
150 Adhesive element
200 Insertion device
201 Cap part
201a Sensor assembly carrier
201b Piercing element carrier guide
202 Base part
203 Piercing element carrier
220 Skin contact surface
230 Coupling structure
240 Activation magnet
250 Insertion device housing
251 Resilient element
252 Spring
253 Activator
260 Piercing element
300 Remote device
I Insertion direction
R Retraction direction
S Patient's skin

What is claimed is:

1. An analyte measurement kit, comprising:
a sensor assembly having a transcutaneous sensor and a controller;
the controller including a battery configured for powering the sensor assembly and a magnetic sensor configured to generate an activation signal in dependence of a magnetic field,
wherein the controller switches from a pre-operative state into an operative state upon generation of the activation signal;
an inserter,
wherein the inserter and the sensor assembly comprise complementary couplers for releasable coupling;
wherein the inserter is configured to execute an insertion movement that advances the sensor assembly from a retracted position in which the transcutaneous sensor is recessed behind a skin contact surface of the inserter into an advanced position in which the transcutaneous sensor projects beyond the skin contact surface, the insertion movement including subsequently retracting a piercing element from the skin, the insertion movement being complete before the inserter is removed from the sensor assembly;

further wherein the inserter includes an activation magnet, and wherein the inserter executing the insertion movement is configured to cause a change of a magnetic coupling between the activation magnet and the sensor assembly to thereby generate the activation signal.

2. The analyte measurement kit according to claim 1, wherein the sensor assembly includes a sensor housing encapsulating the controller and the transcutaneous sensor projects from the sensor housing.

3. The analyte measurement kit according to claim 1, wherein the inserter includes the piercing element coupled with the transcutaneous sensor in the retracted position, wherein the insertion movement includes advancing the piercing element together with the sensor assembly from the retracted position into the advanced position, followed by retracting only the piercing element into the retracted position.

4. The analyte measurement kit according to claim 3, wherein the activation magnet is coupled with the piercing element to move relative to the sensor assembly when retracting the piercing element into the retracted position.

5. The analyte measurement kit according to claim 4, wherein the activation magnet is coupled to or included in the piercing element.

6. The analyte measurement kit according to claim 1, wherein the inserter has an inserter housing and the activation magnet is rigidly coupled to the inserter housing.

7. The analyte measurement kit according to claim 6, wherein the activation magnet is positioned such that a distance between the activation magnet and the magnetic sensor increases upon advancing the sensor assembly into the advanced position to thereby generate the activation signal.

8. The analyte measurement kit according to claim 6, wherein the activation magnet is positioned such that a distance between the activation magnet and the magnetic sensor decreases upon advancing the sensor assembly into the advanced position to thereby generate the activation signal.

9. The analyte measurement kit according to claim 1, wherein the magnetic sensor includes a coil.

10. The analyte measurement kit according to claim 1, wherein the magnetic sensor includes a Hall effect sensor.

11. The analyte measurement kit according to claim 1, wherein the activation magnet and the magnetic sensor are aligned in a coupled state of the sensor assembly and inserter.

12. The analyte measurement kit according to claim 11, wherein the activation magnet and the magnetic sensor are coaxially aligned in the coupled state of the sensor assembly and inserter.

13. The analyte measurement kit according to claim 1, wherein the controller includes a wireless communication interface and wherein the controller is configured, upon being switched into the operative state, to pair with a remote device for data communication via the wireless communication interface.

14. The analyte measurement kit according to claim 1, wherein the sensor assembly in the operative state is configured to execute analyte measurements.

15. The analyte measurement kit according to claim 1, wherein the analyte is glucose.

16. A method for switching a sensor assembly from a pre-operative state into an operative state, comprising:

providing an analyte measurement kit according to claim 1; and executing the insertion routine, the insertion routine including changing the magnetic coupling between the activation magnet and the sensor assembly to thereby generate the activation signal.

* * * * *